US00PP11645P

United States Patent [19]

Wells

[11] Patent Number: Plant 11,645

[45] Date of Patent: Nov. 21, 2000

[54] MINIATURE ROSE PLANT NAMED 'WELQUEEN'

[76] Inventor: Verlie W. Wells, 471 Lucy Kelly Rd., Brighton, Tenn. 38011

[21] Appl. No.: 09/210,007

[22] Filed: Dec. 11, 1998

[51] Int. Cl.[7] ..... A01H 5/00

[52] U.S. Cl. ..... Plt./124; Plt./117

[58] Field of Search ..... Plt./117, 124

[56] References Cited

U.S. PATENT DOCUMENTS

P.P. 10,828 3/1999 Tucker ..... Plt./124

*Primary Examiner*—Howard J. Locker

[57] ABSTRACT

This invention relates to a new and distinct variety of miniature rose plant primarily identified by its white buds and flowers, hybrid tea form and glossy green foliage.

1 Drawing Sheet

The present invention relates to a new and distinct variety of hardy, dwarf, bush type rose plant of the miniature class; the variety being primarily characterized — as to novelty — by buds and flowers of a uniform white color which generally are of exhibition (Hybrid Tea) form.

The variety is further characterized by:

An abundance of bloom, with flowers often borne singly and also several to the stem in loose clusters.

Slight sweet fragrance.

A plant which is vigorous, bushy, upright shape with medium growth habit and leathery and glossy foliage.

The plant, which has an average height of 18 to 30 inches, can easily be maintained at lesser height by occasional trimming.

A plant which grows and blooms satisfactorily both in the greenhouse and outdoors; is good for growing in pots; and provides excellent garden decoration as well as cut flowers.

The present variety of miniature rose was originated by me in my greenhouse located at Brighton, Tenn. under conditions of careful control and observation, as a cross between 'Miss Pearl' (a non-patented commercial seedling) as the seed parent and 'Pacesetter' (U.S. Plant Pat. No. 4,513) as the pollen parent.

Subsequent to origination of the variety, I successfully asexually reproduced it at my greenhouse, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The Royal Horticultural Society Colour Chart, except where common terms of color definition are employed.

Class: Miniature. Variety identification: WELqueen (Commerical synonym: Memphis Queen).

FLOWER

Observations made from specimens grown in a garden environment at Brighton, Tenn. in April 1995 through October 1998.

Blooming habit: Continuous.

Bud:

*Size.*—¾ to 1 inch long when the petals start to unfurl.

*Form.*—The bud form is long and tapered.

*Color.*—When the sepals first divide, bud color Is Yellow Green Group 145D.

*Sepals.*—Color: Light to medium green. Inner surface Yellow Green Group 145B. Outer surface Yellow Green Group 137D. Surface texture: Mostly smooth. Number: Usually 5 (sometimes 4) with some foliaceous appendages.

*Peduncle.*—Length: Medium to Long. 1½ to 1¾ inch. Surface: Smooth. Strength: Stiff and strong. Upright. Color: Yellow Green Group 145A.

Bloom:

*Size.*—Small; Average open size is 1¾ to 2¼ inches.

*Borne.*—Singly and sometimes in clusters of 2 to 5 flowers.

*Stems.*—Strong. Begins with a reddish tint and quickly turns to Green Group 138A.

*Form.*—High centered; Reflexed petals; Exhibition; When fully open stamens show.

*Petalage.*—Double; Number of petals under normal conditions: 45–58. Arranged regularly plus some small petaloids. Petals have excellent substance.

*Color.*—The petals' upper and lower side is White Group 155D, edge of new petals when opening (center of bloom) sometimes tinged with Red-Purple Group 63C.

*Variegations.*—None.

*Discoloration.*—The general tonality at the end of the first day: No change. At the end of the third day: No Change.

*Fragrance.*—Faint, sweet.

Reproductive parts:

*Anthers.*—Size: Medium; Quantity: Few; Color:Orange Group 28B; Arrangement: Regular around styles.

*Filaments.*—Varying length, short to medium long. Yellow Green Group 145C.

*Pollen.*—Quantity: Very Slight; Color: Golden yellow.

*Styles.*—Color: Yellow Green Group 145A.

*Stigmas.*—Color: Yellow Green Group 145D.

*Ovaries.*—All enclosed in calyx.

*Hips.*—None: Female reproductive system appears to be sterile.

*Seeds.*—Has not demonstrated the ability to produce seeds.

Growth:

*Habit.*—Dwarf; bushy; vigorous to 30 inches.

Foliage:

*Leaflets.*—Number on normal mid-stem leaves: 5 or 7.

*Size.*—Medium; Leaflets vary in length from ½ to 2¼ inches.

*Quantity.*—Abundant.

*Color.*—New foliage: Lower Surface Yellow Green Group 146B; reddish overcast and reddish serrated edge; upper surface Yellow Green Group 146A.

*Old foliage.*—Upper surface: Yellow Green Group 147A. Lower surface: Yellow Green Group 147C.

Leaflets:

*Shape.*—Pointed oval.

*Texture.*—Leathery; glossy.

*Edge.*—Serrated.

*Serration.*—Single, small.

*Petiole rachis.*—Smooth with Yellow Green Group 147C coloration.

*Petiole underside.*—Smooth.

*Stipules.*—Medium to short length (½ to ⅝ inch).

Wood:

*New wood.*—Color: Reddish but turns light green very quickly. Reddish thorns.

*Old wood.*—Color: Yellow Green Group 147B. Bark Smooth.

Prickles:

*Quantity.*—Medium; Ordinary.

*Form.*—Varying sizes from small prickles to medium thorns; Medium thorn size (3/16 to ¼ inch); Prickles project straight from stem.

*Color.*—Grey Orange Group 177D.

Disease resistance: Better than average resistance to Blackspot and Powdery mildew.

Winter hardiness: Hardy to zone 5A. (−15 to −20 F.).

The miniature rose plant and its flowers as herein described may vary in slight detail due to climatic, soil and cultural conditions under which the variety may be grown; the present description being of the variety as grown at Brighton, Tenn.

I claim:

1. A new and distinct variety of miniature rose plant of hardy, dwarf, upright habit, substantially as illustrated and described, characterized by buds and flowers of exhibition form, essentially white in color, with reverse same (white), and further characterized by a plant of bushy shape, vigorous, with the main stems and shoots being moderately thorny, the said plant being easy to propagate from cuttings, with an abundance of flowers borne singly or several per stem.

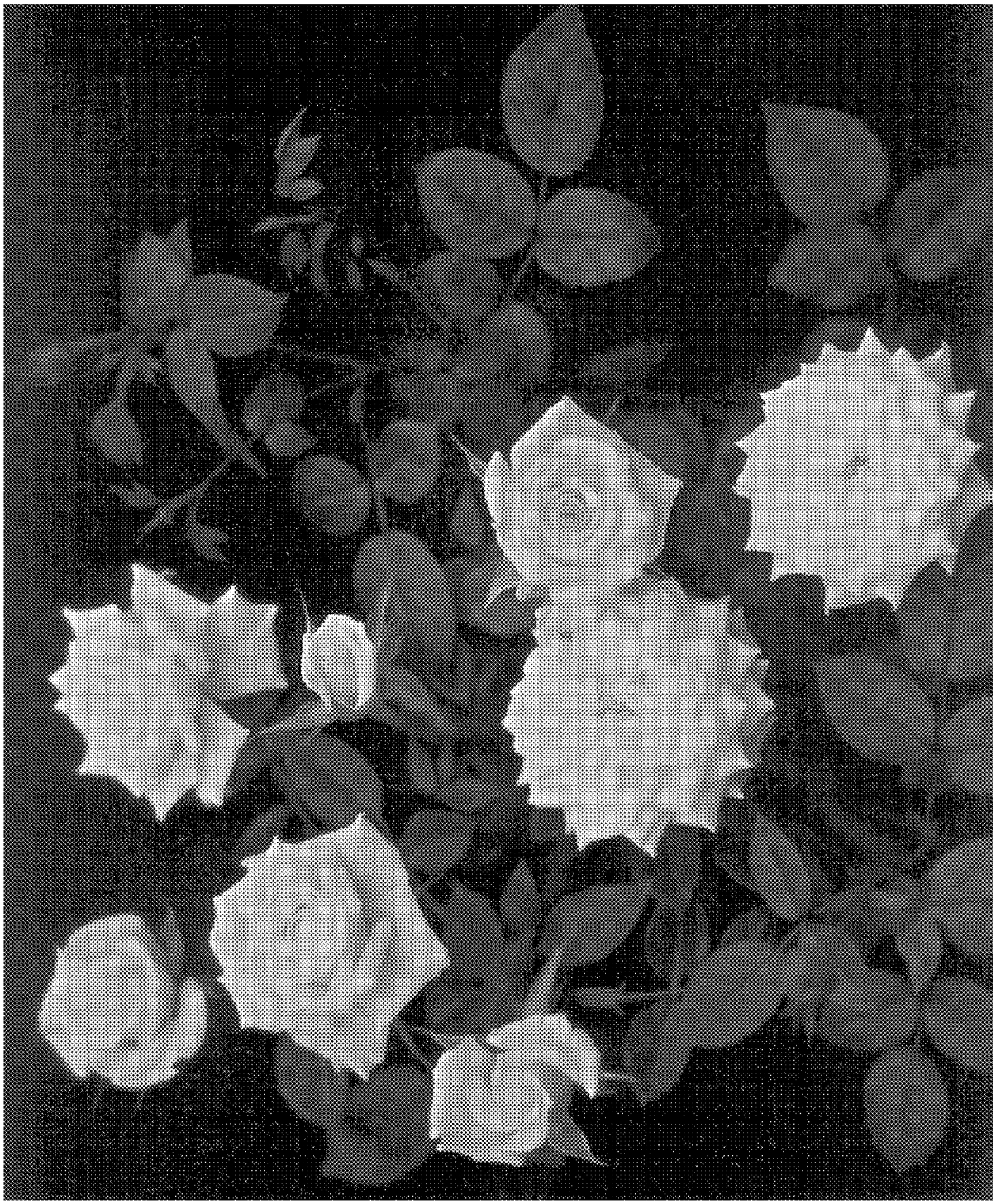

* * * * *